(12) United States Patent
Zheng et al.

(10) Patent No.: US 7,785,259 B2
(45) Date of Patent: Aug. 31, 2010

(54) DETECTION OF MOTION IN VIBRO-ACOUSTOGRAPHY

(75) Inventors: Yi Zheng, Sartell, MN (US); Wei Tan, St. Cloud, MN (US); James Fowler Greenleaf, Rochester, MN (US); Shigao Chen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1139 days.

(21) Appl. No.: 10/956,461

(22) Filed: Oct. 1, 2004

(65) Prior Publication Data

US 2005/0165306 A1 Jul. 28, 2005

Related U.S. Application Data

(60) Provisional application No. 60/508,371, filed on Oct. 3, 2003.

(51) Int. Cl.
*A61B 8/00* (2006.01)
(52) U.S. Cl. .................. 600/438; 600/441; 600/442; 600/444; 601/2; 606/128; 73/1.82; 73/1.89
(58) Field of Classification Search ............. 600/437, 600/438, 441, 444, 442; 601/2; 606/128; 73/1.82, 1.89
See application file for complete search history.

(56) References Cited

U.S. PATENT DOCUMENTS

| 5,487,306 | A | * | 1/1996 | Fortes ..................... 73/597 |
| 5,606,971 | A | | 3/1997 | Sarvazyan |
| 5,810,731 | A | | 9/1998 | Sarvazyan |
| 5,903,516 | A | | 5/1999 | Greenleaf et al. |
| 5,991,239 | A | | 11/1999 | Fatemi-Booshehri et al. |
| 6,045,504 | A | * | 4/2000 | Muzilla et al. ............ 600/437 |
| 6,068,597 | A | * | 5/2000 | Lin ........................ 600/443 |
| 6,245,016 | B1 | * | 6/2001 | Daft et al. ................. 600/443 |
| 6,764,448 | B2 | | 7/2004 | Trahey et al. |
| 6,951,544 | B2 | | 10/2005 | Trahey et al. |
| 6,984,209 | B2 | * | 1/2006 | Hynynen et al. ........... 600/438 |

OTHER PUBLICATIONS

S. Chen, et al., Complex Stiffness Quantificatin Using Ultrasound Stimulated Vibrometry, 2003 IEEE Ultrasonics Symposium pp. 941-944.
Xiaoming Zhang, et al., Excitation and Measurement of Flexural Waves in Arterial Vessels, 2003 IEEE Ultrasonics Symposium pp. 1883-1886.
Xiaoming Zhang, et al Excitation and Measurement Of Flexural Waves in Arterial Vessels, 2003 IEEE Ultrasonics Symposium pp. 1883-1886.
S.Chen et al, Complex Stiffness Quantification Using Ultrasound Stimulated Vibrometry, 2003 IEEE Ultrasonics Symposium pp. 941-944.

* cited by examiner

*Primary Examiner*—Long V Le
*Assistant Examiner*—Ellsworth Weatherby
(74) *Attorney, Agent, or Firm*—Qualres & Brady LLP

(57) ABSTRACT

Harmonic motion is produced in a subject using vibro-acoustography. An ultrasonic imaging system repetitively interrogates the subject and the Doppler shift in the reflected echo signals is analyzed to measure the phase and amplitude of harmonic motion produced in the subject at different prescribed frequencies. Shear wave propagation through the subject is determined from this information and mechanical properties related to "stiffness" of the subject are determined. A Kalman filter is employed in the phase and amplitude measurement to extract the harmonic motion information from background noise.

15 Claims, 3 Drawing Sheets

DETECTION OF MOTION IN VIBRO-ACOUSTOGRAPHY

CROSS-REFERENCE TO RELATED APPLICATIONS

This application claims the benefit of U.S. Provisional patent application Ser. No. 60/508,371 filed on Oct. 3, 2003 and entitled "Motion Detection For Vibroacoustography".

STATEMENT REGARDING FEDERALLY SPONSORED RESEARCH

This invention was made with government support under Grant No. EB002640 awarded by the National Institutes of Health National Institute of Biomedical Imaging and Bioengineering. The government has certain rights in this invention.

BACKGROUND OF THE INVENTION

The field of the invention is coherent imaging using vibratory energy, such as ultrasound and, in particular, vibro-acoustography.

There are a number of modes in which ultrasound can be used to produce images of objects. The ultrasound transmitter may be placed on one side of the object and the sound transmitted through the object to the ultrasound receiver placed on the other side ("transmission mode"). With transmission mode methods, an image may be produced in which the brightness of each pixel is a function of the amplitude of the ultrasound that reaches the receiver ("attenuation" mode), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver ("refraction", "backscatter" or "echo" mode).

There are a number of well known backscatter methods for acquiring ultrasound data. In the so-called "A-scan" method, an ultrasound pulse is directed into the object by the transducer and the amplitude of the reflected sound is recorded over a period of time. The amplitude of the echo signal is proportional to the scattering strength of the refractors in the object and the time delay is proportional to the range of the refractors from the transducer. In the so-called "B-scan" method, the transducer transmits a series of ultrasonic pulses as it is scanned across the object along a single axis of motion. The resulting echo signals are recorded as with the A-scan method and either their amplitude or time delay is used to modulate the brightness of pixels on a display. With the B-scan method, enough data are acquired from which an image of the refractors can be reconstructed.

Ultrasonic transducers for medical applications are constructed from one or more piezoelectric elements sandwiched between a pair of electrodes. Such piezoelectric elements are typically constructed of lead zirconate titanate (PZT), polyvinylidene difluoride (PVDF), or PZT ceramic/polymer composite. The electrodes are connected to a voltage source, and when a voltage is applied, the piezoelectric elements change in size at a frequency corresponding to that of the applied voltage. When a voltage pulse is applied, the piezoelectric element emits an ultrasonic wave into the media to which it is coupled at the frequencies contained in the excitation pulse. Conversely, when an ultrasonic wave strikes the piezoelectric element, the element produces a corresponding voltage across its electrodes. Typically, the front of the element is covered with an acoustic matching layer that improves the coupling with the media in which the ultrasonic waves propagate. In addition, a backing material is disposed to the rear of the piezoelectric element to absorb ultrasonic waves that emerge from the back side of the element so that they do not interfere. A number of such ultrasonic transducer constructions are disclosed in U.S. Pat. Nos. 4,217,684; 4,425,525; 4,441,503; 4,470,305 and 4,569,231.

When used for ultrasound imaging, the transducer typically has a number of piezoelectric elements arranged in an array and driven with separate voltages (apodizing). By controlling the time delay (or phase) and amplitude of the applied voltages, the ultrasonic waves produced by the piezoelectric elements (transmission mode) combine to produce a net ultrasonic wave focused at a selected point. By controlling the time delay and amplitude of the applied voltages, this focal point can be moved in a plane to scan the subject.

The same principles apply when the transducer is employed to receive the reflected sound (receiver mode). That is, the voltages produced at the transducer elements in the array are summed together such that the net signal is indicative of the sound reflected from a single focal point in the subject. As with the transmission mode, this focused reception of the ultrasonic energy is achieved by imparting separate time delay (and/or phase shifts) and gains to the signal from each transducer array element.

This form of ultrasonic imaging is referred to as "phased array sector scanning", or "PASS". Such a scan is comprised of a series of measurements in which the steered ultrasonic wave is transmitted, the system switches to receive mode after a short time interval, and the reflected ultrasonic wave is received and stored. Typically, the transmission and reception are steered in the same direction ($\theta$) during each measurement to acquire data from a series of points along a scan line. The receiver is dynamically focused at a succession of ranges (R) along the scan line as the reflected ultrasonic waves are received. The time required to conduct the entire scan is a function of the time required to make each measurement and the number of measurements required to cover the entire region of interest at the desired resolution and signal-to-noise ratio. For example, a total of 128 scan lines may be acquired over a 90° sector, with each scan line being steered in increments of 0.70. A number of such ultrasonic imaging systems are disclosed in U.S. Pat. Nos. 4,155,258; 4,155,260; 4,154,113; 4,155,259; 4,180,790; 4,470,303; 4,662,223; 4,669,314 and 4,809,184.

Vibro-acoustography is an elasticity modality that vibrates tissue using ultrasound radiation force. The radiation force is generated by focusing two ultrasound beams on the object. These two ultrasound beams have slightly different frequencies and the tissue at the focal point vibrates at the difference frequency. The vibration frequency can be easily changed and the "stiffness" of the tissue at different frequencies can be measured. The tissue is scanned in a raster manner and its acoustic emission is detected by a hydrophone. The acquired emission data may be processed to reconstruct an image, which is related to the stiffness of the tissue. The details of the vibro-acoustography is described in U.S. Pat. No. 5,903,516 entitled "Acoustic force generator for detection, imaging and information transmission using the beat signal of multiple intersecting sonic beams" and U.S. Pat. No. 5,991,239 entitled "Confocal acoustic force generator".

A method was recently proposed to solve for the complex stiffness of a homogeneous medium or an artery by measuring shear wave speed dispersion. An oscillatory radiation force is applied to the subject using vibro-acoustography to generate shear waves of various frequencies. The speed of these shear waves is measured from shifts in phase detected over the distance propagated. Measurements of shear wave speed at multiple frequencies are then fit with appropriate theoretical models to solve for the shear elasticity and viscosity of the object as described in Ph.D. Thesis: Direct Methods for Dynamic Elastography Reconstruction: Optimal Inversion of the Interior Helmholtz Problem, Travis Oliphant, Ph.D. May 2001 and Ph.D. Thesis: Shear Property Characterization of Viscoelastic Media Using Vibrations Induced by Ultrasound Radiation, Shigao Chen, Ph.D. June 2002). Although the results are very promising, detection of the shear wave is achieved by an optical method, which limits its medical application because soft tissues are opaque.

SUMMARY OF THE INVENTION

The present invention is a vibro-acoustic system for measuring mechanical properties of opaque subjects such as tissue which includes an acoustic force generator that imparts harmonic motion to the subject at a prescribed frequency, an ultrasonic system for interrogating points in the subject with ultrasonic pulses and receiving echo signals therefrom which indicate the amplitude and phase of the harmonic motion at the points. The echo signals are processed to extract the harmonic motion phase information, and from this a mechanical property of the subject is calculated.

A more specific aspect of the invention is the method used to estimate the harmonic phase information in the echo signals. The echo signals are quadrature detected and the arctangent of the ratio of the Q and I components acquired at each point are calculated to produce a measured harmonic signal in slow time. The desired harmonic signal is modeled by a differential equation and the phase and amplitude parameters in this model are recursively estimated in a Kalman filter until the mean square error between the model and the measured harmonic signal is minimized.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

GENERAL DESCRIPTION OF THE INVENTION

Figure 1:
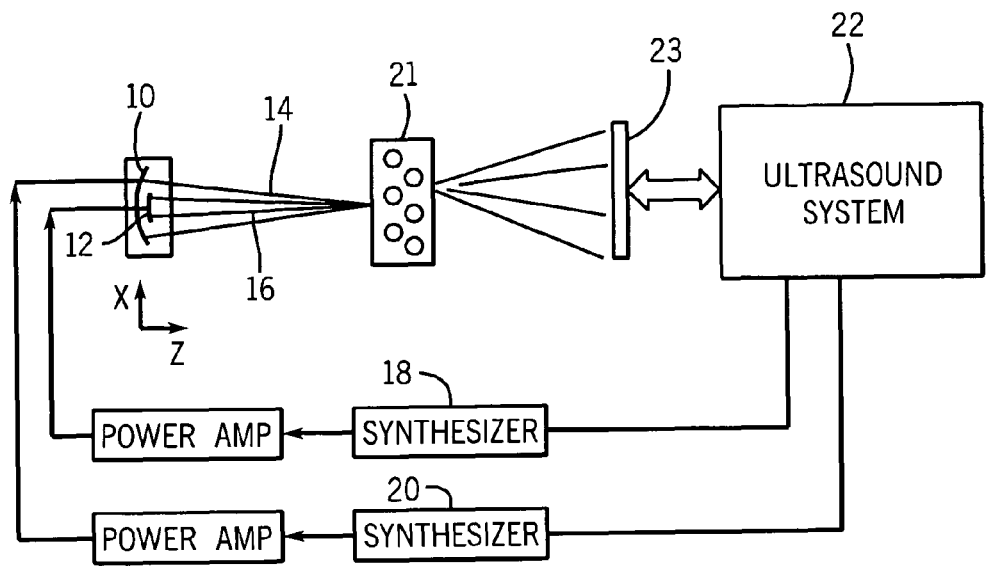
FIG. 1 is a block diagram of a vibro-acoustic system which employs the present invention.

The present invention is a vibro-acoustic system for measuring the mechanical properties of opaque subjects such as tissue. Where the subject tissue is buried deeply beneath other tissue, optical methods for measuring the very small harmonic motions of the subject tissue cannot be used. This problem is solved by employing an ultrasonic imaging system that interrogates the subject tissue with a pulsed ultrasound beam and examines the resulting echo signals to measure the phase and amplitude of the harmonic motion imparted to the subject tissue. The challenge is to extract this information from the echo signals where the amplitude of the harmonic motion is at the submicron level.

The displacement of a point in harmonic motion of tissues can be represented in the form of, $$D(t) = D_0 \sin(\omega_s t + \phi_s) \qquad (1)$$

The velocity of the motion is:

$$v(t) = \frac{dD(t)}{dt} = v_0 \cos(\omega_s t + \phi_s) \qquad (2)$$

where $v_0 = D_0 \omega_s$.

When a pulse echo ultrasound system is focused on the tissue motion, the tissue motion is represented in the echo signals as oscillatory Doppler shifts in the received signals.

$$r(t_f, t_s) = A(t_f, t_s) \cos\left(\int \left(\omega_f + \frac{2v(t)}{c}\omega_f \cos\theta\right)dt\right) \qquad (3)$$
$$= A(t_f, t_s) \cos(\omega_f t_f + \phi_f + \beta \sin(\omega_s t_s + \phi_s))$$

where $t_f$ is fast time representing depth, $t_s$ is slow time representing repetitive pulses, $\omega_f$ is transmitting center frequency, $\omega_s$ is the tissue vibration frequency, $\phi_s$ is the tissue vibration phase, and $\theta$ is an angle between the ultrasound beam and direction of tissue motion. The modulation index is:

$$\beta = \frac{2v_0 \omega_f \cos(\theta)}{\omega_s c} \qquad (4)$$

where c is the sound speed in the tissue.

With quadrature demodulation of the received echo signal, we have in-phase and quadrature terms:

$$I(t_f, t_s) = A(t_f, t_s)\cos(\beta \sin(\omega_s t_s + \phi_s) + \phi_f + \phi_0) \qquad (5)$$

$$Q(t_f, t_s) = -A(t_f, t_s)\sin(\beta \sin(\omega_s t_s + \phi_s) + \phi_f + \phi_0) \qquad (6)$$

where $\phi_0$ is a constant phase added during the quadrature demodulation to maintain $I(t_f, t_s)$ to be either all positive or all negative in slow time at a location. Thus, $$s(t_f, t_s) = -\tan^{-1}(Q(t_f, t_s)/I(t_f, t_s)) \qquad (7)$$

$$y(t_s) = s(t_f, t_s) - \bar{s}(t_f, t_s) = \beta \sin(\omega_s t_s + \phi_s) \qquad (8)$$

where $\bar{s}(t_f, t_s)$ is a mean value of $s(t_f, t_s)$ in slow time. If the sampling frequency in fast time is high, $I(t_f, t_s)$ and $Q(t_f, t_s)$ can be averaged with a limited length in fast time to reduce noise before $s(t_f, t_s)$ is calculated.

A bandpass filter (BPF) centered at the vibration frequency can improve $y(t_s)$ by reducing noise and distortions.

The amplitude can be directly estimated from $y(t_s)$, $$\beta = \sqrt{2}\sigma_y \qquad (9)$$

where $\sigma_y$ is a standard deviation of $y(t_s)$.

The phase and amplitude in Equation (8) can be directly obtained by another quadrature demodulation at the vibration frequency in the direction of the slow time, $$I(t_s) = \beta \cos(\phi_s) \quad (10)$$

$$Q(t_s) = \beta \sin(\phi_s) \quad (11)$$

$$\beta(t_s) = \sqrt{I^2(t_s) + Q^2(t_s)} \quad (12)$$

$$\phi_s(t_s) = a\tan(Q(t_s)/I(t_s)) \quad (13)$$

The amplitude of the oscillatory Doppler shifts can also be directly measured by applying a turbulence estimation method to the $r(t_f, t_s)$ to estimate the variance of motion velocity.

In practice, the data will be noisy and have a stochastic nature. Therefore, a Kalman filter process is employed to recursively estimate the phase and amplitude. As described by R. G. Brown and P. Y. C. Hwang in "Introduction To Random Signals And Applied Kalman Filtering", 3$^{rd}$ Edition, John Wily & sons, 1997, a Kalman filter is a numerical method used to track a time-varying signal in the presence of noise. If the signal can be characterized by some number of parameters that vary slowly with time, then Kalman filtering can be used to tell how incoming raw measurements should be processed to best estimate those parameters as a function of time. In this application, a Kalman filter extracts the desired harmonic motion from random and noisy measurement data with known vibration frequency and unknown vibration amplitude and phase. Equation (8) can be represented by a 2$^{nd}$ order differential equation, $$\frac{d^2 y(t_s)}{dt_s^2} + \omega_s^2 y(t_s) = 0 \quad (14)$$

which can be transformed to a 2$^{nd}$ order state space form:

$$\begin{bmatrix} x_k(1) \\ x_k(2) \end{bmatrix} = \begin{bmatrix} 1 & 0 \\ 0 & 1 \end{bmatrix} \begin{bmatrix} x_k(1) \\ x_k(2) \end{bmatrix} \text{ or } x_k = \Phi x_k. \quad (15)$$

The measurement equation is:

$$y(t_s) = \beta \sin(\omega_s t_s)\cos \phi_s + \beta \cos(\omega_s t_s)\sin \phi_s \quad (16)$$
$$= [\sin(\omega_s t_s), \cos(\omega_s t_s)][\beta \cos \phi_s, \beta \sin \phi_s]^T$$
$$y(k) = [h_k(1), h_k(2)][x_k(1), x_k(2)]^T \text{ or,}$$
$$y(k) = H_k x_k + n(k)$$

where $t_s = k/f_{PRF}$ and n(k) is a white noise sequence having a variance R. $f_{PRF}$ is the pulse repetition frequency. Thus the amplitude and phase parameters of the desired harmonic signal can be found:

$$\beta(k) = \sqrt{x_k^2(1) + x_k^2(2)}$$

$$\phi_s(k) = \tan^{-1}(x_k(2)/x_k(1)) \quad (17)$$

The estimation $\hat{x}(k)$ for x(k) is given by minimizing the mean square error:

$$P_k = E[(x_k - \hat{x}_k)(x_k - \hat{x}_k)^T] \quad (18)$$

The estimated state variables in the final steps of Kalman filtering are averaged for the amplitude and phase. The filtering steps are listed below:

1. Initializing:

$$P_1^- = R, \hat{x}_1^- = E[x_1] \quad (19)$$

2. Calculating Kalman gain at k$^{th}$ step:

$$G_k = P_k^- H_k^T (H_k P_k^- H_k^T + R)^{-1} \quad (20)$$

3. Updating the state estimation:

$$\hat{x}_k = \hat{x}_{k-1}^- + G_k(y(k) - H_k \hat{x}_{k-1}^-) \quad (21)$$

4. Calculating the error covariance matrix:

$$P_k = (I - G_k H_k) P_k^- \quad (22)$$

5. Project ahead:

$$\hat{x}_{k+1}^- = \Phi_k \hat{x}_k \quad (23)$$

$$P_{k+1}^- = \Phi_k P_k \Phi_k^T + Q \quad (24)$$

where Q is zero in this application and P is an estimation error covariance matrix that describes the estimation accuracy.

The error covariance matrix provide by the Kalman filter is:

$$P = E[(x - \hat{x})(x - \hat{x})] = \begin{pmatrix} \sigma_{x1}^2 & \sigma_{x2x1} \\ \sigma_{x1x2} & \sigma_{x2}^2 \end{pmatrix} \quad (25)$$

where the diagonal elements represent variance of estimation errors for $x_1$ and $x_2$.

$$x_1 = \beta \cos \phi_s \quad (26)$$

$$x_2 = \beta \sin \phi_s. \quad (27)$$

The relations between the state variables and the amplitude $\beta$ and estimated phase $\phi_s$ of the harmonic motion are, $$\hat{\beta} = \sqrt{x_1^2 + x_2^2} \quad (28)$$

$$\hat{\phi}_s = a\tan\frac{x_2}{x_1} \quad (29)$$

If $y = f(x_1, x_2)$ and $\sigma_{x1}, \sigma_{x2}$ are given, then the variance of y is, $$\sigma_y = \sqrt{\left(\frac{\partial f}{\partial x_1}\right)^2 \sigma_{x1}^2 + \left(\frac{\partial f}{\partial x_2}\right)^2 \sigma_{x2}^2} \quad (30)$$

For $\sigma_\beta: f = \sqrt{x_1^2 + x_2^2}$ $$\frac{\partial f}{\partial x_1} = \frac{\partial \sqrt{x_1^2 + x_2^2}}{\partial x_1} = \frac{1}{2}\left(\frac{1}{\sqrt{x_1^2 + x_2^2}}\right) 2x_1 = \frac{x_1}{\sqrt{x_1^2 + x_2^2}} \quad (31)$$

$$\frac{\partial f}{\partial x_2} = \frac{\partial \sqrt{x_1^2 + x_2^2}}{\partial x_2} = \frac{1}{2}\left(\frac{1}{\sqrt{x_1^2 + x_2^2}}\right) 2x_2 = \frac{x_2}{\sqrt{x_1^2 + x_2^2}}. \quad (32)$$

Therefore, the standard deviation of estimation errors of amplitude estimates is:

$$\sigma_\beta = \sqrt{\left(\frac{\partial f}{\partial x_1}\right)^2 \sigma_{x1}^2 + \left(\frac{\partial f}{\partial x_2}\right)^2 \sigma_{x2}^2} \quad (33)$$

$$= \sqrt{\left(\frac{x_1}{\sqrt{x_1^2 + x_2^2}}\right)^2 \sigma_{x1}^2 + \left(\frac{x_2}{\sqrt{x_1^2 + x_2^2}}\right)^2 \sigma_{x2}^2}$$

$$= \sqrt{\frac{x_1^2 \sigma_{x1}^2 + x_2^2 \sigma_{x2}^2}{x_1^2 + x_2^2}}$$

For $\sigma_{\phi s}: f = a\, \tan\left(\frac{x_2}{x_1}\right)$ $$\frac{\partial f}{\partial x_1} = \frac{1}{1 + \left(\frac{x_2}{x_1}\right)^2}\left(-\frac{x_2}{x_1^2}\right) = -\frac{x_2}{x_1^2 + x_2^2} \quad (34)$$

$$\frac{\partial f}{\partial x_2} = \frac{1}{1 + \left(\frac{x_2}{x_1}\right)^2}\left(\frac{1}{x_1}\right) = \frac{x_1}{x_1^2 + x_2^2} \quad (35)$$

$$\sigma_{\phi s} = \sqrt{\left(\frac{\partial f}{\partial x_1}\right)^2 \sigma_{x1}^2 + \left(\frac{\partial f}{\partial x_2}\right)^2 \sigma_{x2}^2} \quad (36)$$

$$= \sqrt{\left(-\frac{x_2}{x_1^2 + x_2^2}\right)^2 \sigma_{x1}^2 + \left(\frac{x_1}{x_1^2 + x_2^2}\right)^2 \sigma_{x2}^2}$$

$$= \sqrt{\frac{x_2^2 \sigma_{x1}^2 + x_1^2 \sigma_{x2}^2}{(x_1^2 + x_2^2)^2}}$$

$$= \frac{\sqrt{x_2^2 \sigma_{x1}^2 + x_1^2 \sigma_{x2}^2}}{x_1^2 + x_2^2}$$

The above equation is for the standard deviation of estimation errors of phase estimates. Thus, the Kalman filter also provides a measure of estimation quality.

The above method can be applied to estimate phase $\phi_s$ of tissue vibration propagating over a known distance $\Delta r$. Then, the shear wave speed can be estimated using the phase change $\Delta\phi_s$ over $\Delta r$:

$$c_s = \omega_s \Delta r / \Delta\phi_s \quad (37)$$

which can be used to characterize elasticity and viscosity of the artery.

DETAILED DESCRIPTION OF THE PREFERRED EMBODIMENT

Referring particularly to FIG. 1, a vibro-acoustography system which employs the present invention employs an ultrasonic transducer having two elements 10 and 12 which produce two focused beams 14 and 16 that cross each other at their focal points as described in U.S. Pat. No. 5,991,239. The elements 10 and 12 are driven by respective continuous wave synthesizers 18 and 20 at ultrasonic frequencies $\omega_1$ and $\omega_2$ that differ by a desired beat frequency. The two focused beams 14 and 16 are aimed at target tissue 21 which is to be measured, and in response, the target tissue vibrates, or oscillates, at the difference frequency. These elements thus serve as a force generator which oscillates the target tissues 21 at a prescribed beat frequency.

The vibrations of the target tissue 21 are measured by an ultrasound system 22. As will be described in more detail below, the ultrasound system 22 drives an ultrasonic transducer 23 to apply a focused ultrasound beam to the target tissue 21 and to receive the echo signal reflected by the target tissue 21. The phase and amplitude of these echo signals are processed as described below to measure mechanical properties of the target tissue 21.

Figure 2:
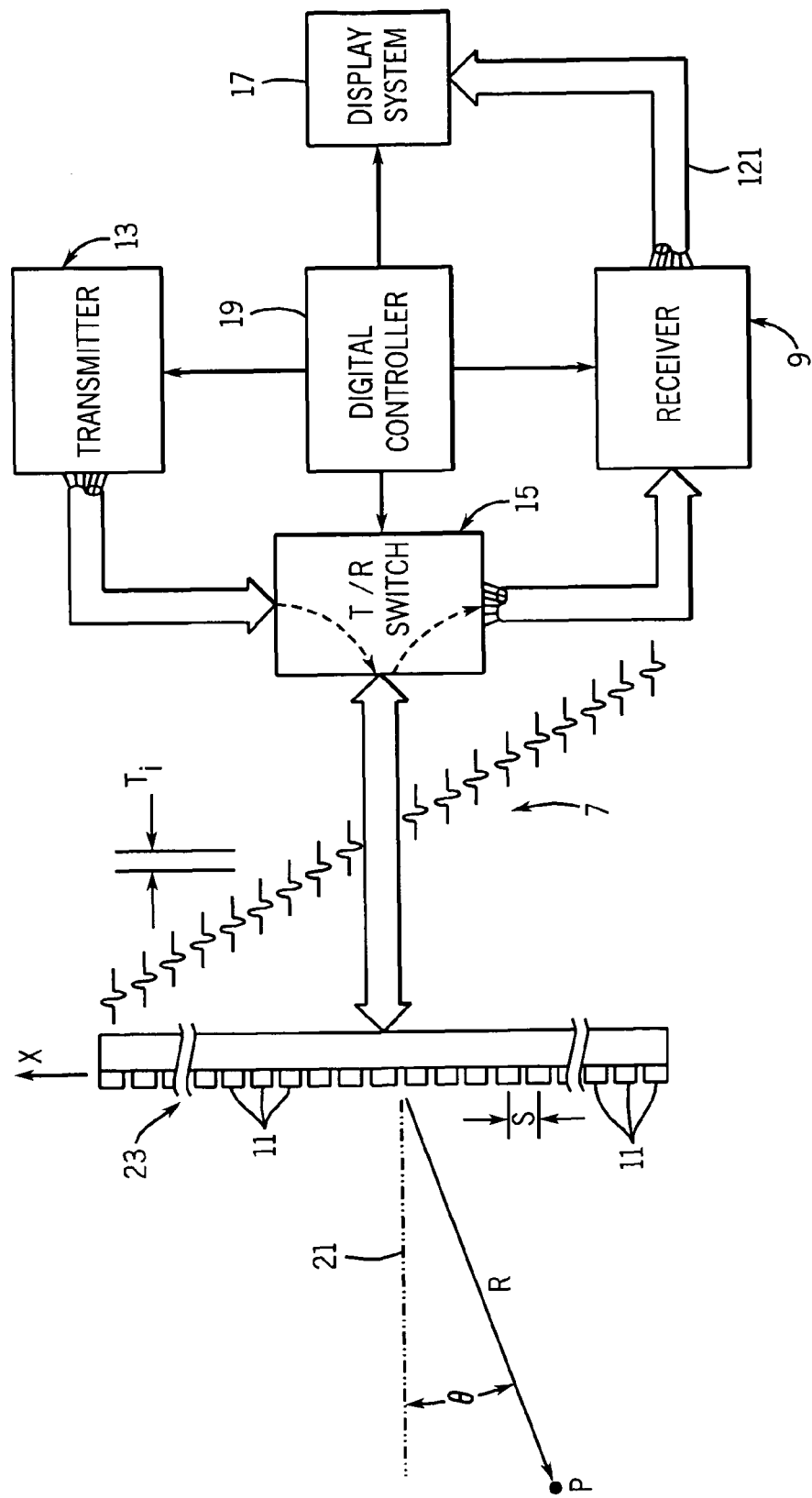
FIG. 2 is a block diagram of an ultrasound imaging system used in the system of FIG. 1.

Referring particularly to FIG. 2, a transducer array 23 is comprised of a plurality of separately driven elements 11 which each produce a burst of ultrasonic energy when energized by a pulse produced by a transmitter 13. The ultrasonic energy reflected back to the transducer array 23 from the subject under study is converted to an electrical signal by each transducer element 11 and applied separately to a receiver 9 through a set of switches 15. The transmitter 13, receiver 9 and the switches 15 are operated under the control of a digital controller 19 responsive to the commands input by the human operator. A complete scan is performed by acquiring a series of echoes in which the switches 15 are set to their transmit position, the transmitter 13 is gated on momentarily to energize each transducer element 11, the switches 15 are then set to their receive position, and the subsequent echo signals produced by each transducer element 11 are applied to the receiver 9. The separate echo signals from each transducer element 11 are combined in the receiver 9 to produce a single echo signal which is employed to produce a line in an image on a display system 17.

The transmitter 13 drives the transducer array 23 such that the ultrasonic energy produced is directed, or steered, in a beam. A B-scan can therefore be performed by moving this beam through a set of angles from point-to-point rather than physically moving the transducer array 23. To accomplish this the transmitter 13 imparts a time delay (Ti) to the respective pulses 20 that are applied to successive transducer elements 11. If the time delay is zero (Ti=0), all the transducer elements 11 are energized simultaneously and the resulting ultrasonic beam is directed along an axis 21 normal to the transducer face and originating from the center of the transducer array 23. As the time delay (Ti) is increased, the ultrasonic beam is directed downward from the central axis 21 by an angle $\theta$.

A sector scan is performed by progressively changing the time delays Ti in successive excitations. The angle $\theta$ is thus changed in increments to steer the transmitted beam in a succession of directions. When the direction of the beam is above the central axis 21, the timing of the pulses 7 is reversed.

Referring still to FIG. 2, the echo signals produced by each burst of ultrasonic energy emanate from reflecting objects located at successive positions (R) along the ultrasonic beam. These are sensed separately by each segment 11 of the transducer array 23 and a sample of the magnitude of the echo signal at a particular point in time represents the amount of reflection occurring at a specific range (R). Due to the differences in the propagation paths between a focal point P and each transducer element 11, however, these echo signals will not occur simultaneously and their amplitudes will not be equal. The function of the receiver 9 is to amplify and demodulate these separate echo signals, impart the proper time delay to each and sum them together to provide a single echo signal which accurately indicates the total ultrasonic energy reflected from each focal point P located at range R along the ultrasonic beam oriented at the angle $\theta$.

To simultaneously sum the electrical signals produced by the echoes from each transducer element 11, time delays are introduced into each separate transducer element channel of the receiver 9. In the case of the linear array 23, the delay introduced in each channel may be divided into two components, one component is referred to as a beam steering time delay, and the other component is referred to as a beam focusing time delay. The beam steering and beam focusing time delays for reception are precisely the same delays (Ti) as the transmission delays described above. However, the focusing time delay component introduced into each receiver channel is continuously changing during reception of the echo to provide dynamic focusing of the received beam at the range R from which the echo signal emanates.

Under the direction of the digital controller 19, the receiver 9 provides delays during the scan such that the steering of the receiver 9 tracks with the direction of the beam steered by the transmitter 13 and it samples the echo signals at a succession of ranges and provides the proper delays to dynamically focus at points P along the beam. Thus, each emission of an ultrasonic pulse results in the acquisition of a series of data points which represent the amount of reflected sound from a corresponding series of points P located along the ultrasonic beam.

By selecting proper time delays, echoes from multiple focused locations can be simultaneously received to measure vibration information from several points of the tissue. The limitation of the lateral resolution of the transducer for two closely located points can be improved by assigning different transmitting codes for different locations.

The display system 17 receives the series of data points produced by the receiver 9 and converts the data to a form producing the desired image. For example, if an A-scan is desired, the magnitude of the series of data points is merely graphed as a function of time. If a B-scan is desired, each data point in the series is used to control the brightness of a pixel in the image, and a scan comprised of a series of measurements at successive steering angles (θ) is performed to provide the data necessary for display of an image.

Figure 3:
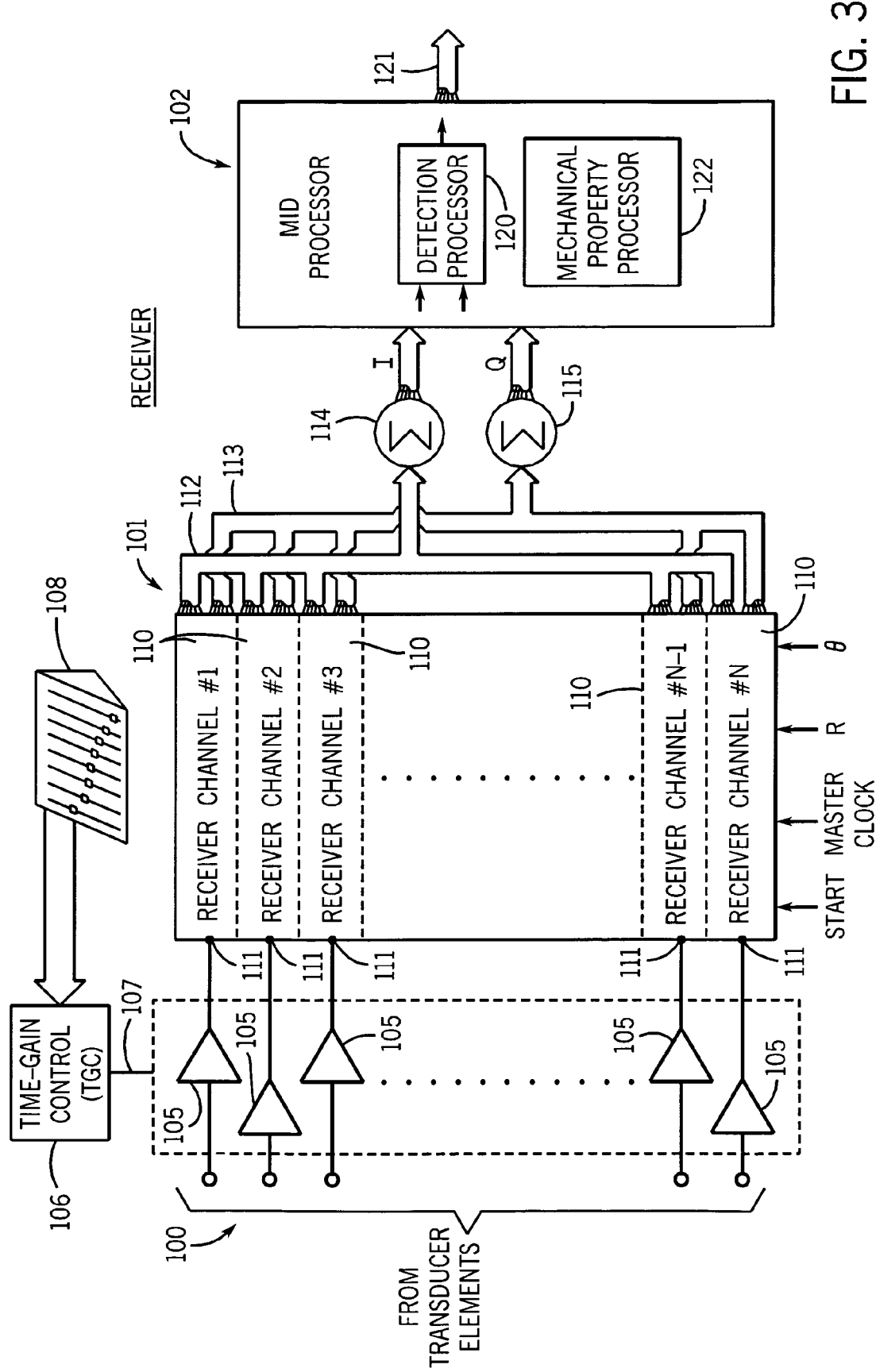
FIG. 3 is a block diagram of a receiver which forms part of the ultrasound imaging system of FIG. 1.

Referring particularly to FIG. 3, the receiver 9 is comprised of three sections: a time-gain control section 100, a beam forming section 101, and a mid processor 102. The time-gain control section 100 includes an amplifier 105 for each of the N=128 receiver channels and a time-gain control circuit 106. The input of each amplifier 105 is connected to a respective one of the transducer elements 11 to receive and amplify the echo signal which it receives. The amount of amplification provided by the amplifiers 105 is controlled through a control line 107 that is driven by the time-gain control circuit 106. As is well known in the art, as the range of the echo signal increases, its amplitude is diminished. As a result, unless the echo signal emanating from more distant reflectors is amplified more than the echo signal from nearby reflectors, the brightness of the image diminishes rapidly as a function of range (R). This amplification is controlled by the operator who manually sets TGC linear potentiometers 108 to values which provide a relatively uniform brightness over the entire range of the sector scan. The time interval over which the echo signal is acquired determines the range from which it emanates, and this time interval is divided into by the TGC control circuit 106. The settings of the potentiometers are employed to set the gain of the amplifiers 105 during each of the respective time intervals so that the echo signal is amplified in ever increasing amounts over the acquisition time interval.

The beam forming section 101 of the receiver 9 includes N=128 separate receiver channels 110. Each receiver channel 110 receives the analog echo signal from one of the TGC amplifiers 105 at an input 111, and it produces a stream of digitized output values on an I bus 112 and a Q bus 113. Each of these I and Q values represents a sample of the echo signal envelope at a specific range (R). These samples have been delayed in the manner described above such that when they are summed at summing points 114 and 115 with the I and Q samples from each of the other receiver channels 110, they indicate the magnitude and phase of the echo signal reflected from a point P located at range R on the steered beam (θ).

For a more detailed description of the receiver 9, reference is made to U.S. Pat. No. 4,983,970 which issued on Jan. 8, 1991 and is entitled "Method And Apparatus for Digital Phase Array Imaging", and which is incorporated herein by reference.

Referring still to FIG. 3, the mid processor section 102 receives the beam samples from the summing points 114 and 115. The I and Q values of each beam sample is a 16-bit digital number which represents the in-phase and quadrature components of the magnitude of the reflected sound from a point (R,θ). The mid processor 102 can perform a variety of calculations on these beam samples, where choice is determined by the type of image to be reconstructed.

For example, a conventional ultrasound image may be produced by a detection processor 120 which calculates the magnitude of the echo signal from its I and Q components:

$$M=\sqrt{I^2+Q^2}.$$

The resulting magnitude values output at 121 to the display system 17 result in an image in which the magnitude of the reflected echo at each image pixel is indicated.

The present invention is implemented by a mechanical property processor 122 which forms part of the mid-processor 102. As will be explained in detail below, this processor 102 receives the I and Q beam samples acquired during a sequence of measurements of the subject tissue 21 and calculates a mechanical property of the tissue 21.

Figure 4:
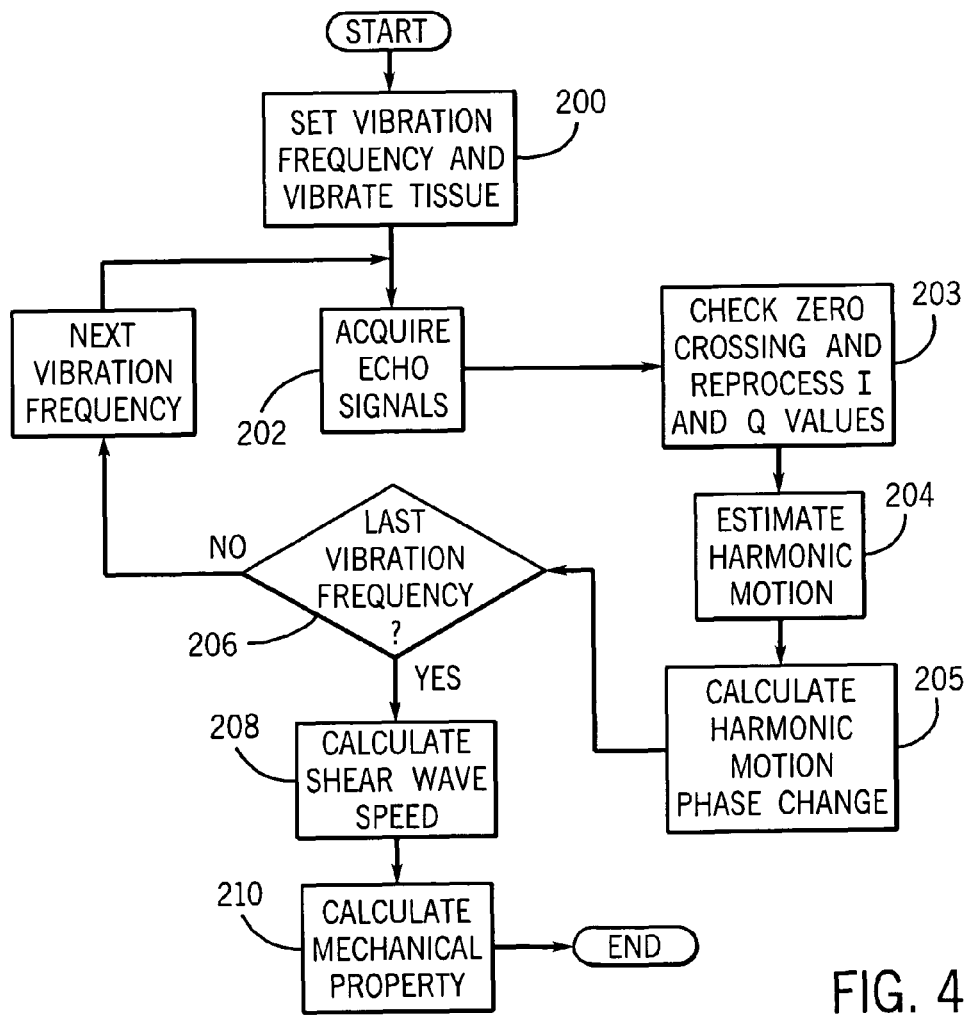
FIG. 4 is a flow chart of the steps performed by a midprocessor which forms part of the receiver of FIG. 3.

Referring particularly to FIG. 4, the mechanical property processor 122 controls the measurements made by the ultrasound system 22, the force generator elements, and it processes the resulting echo signals I and Q to satisfy equations (5) and (6) and to calculate a mechanical property of the target tissues. Such target tissues may be, for example, an artery and the mechanical property may be stiffness. The first step as indicated by process block 200 is to set the beat frequency of the force generator and excite the target tissues 21 with the force generator. As indicated at process block 202 the ultrasound system 22 is then operated to acquire echo signals from the subject tissues at a series of points. When measuring an artery, for example, 100 echoes sampled at a 40 MHz sample rate are acquired at each point, and 11 points spread evenly along 10 to 20 mm of the length of the artery are measured. Eight echo samples at the peak echo amplitude are used to obtain average I and Q values. As described above, it is necessary that all the I values remain either positive or negative in order to properly detect the harmonic signal. As indicated at process block 203, the I values are checked and if a zero crossing occurs, all the I and Q values are reprocessed to add a constant phase $\phi_0$ as indicated above in equations (5) and (6). Phase is added until no zero crossings are detected.

As indicated at process block 204, the amplitude and phase of the tissue motion at each point is then estimated from the acquired I and Q echo samples. As described above there are a number of different methods for accomplishing this, but in the preferred embodiment the arctangent of the ratio of the Q and I beam samples are calculated and the mean value is removed to obtain the harmonic motion in slow time as indicated above in Equations (7) and (8). The harmonic motion is modeled by a second order differential equation with random amplitude and phase and the known beat frequency. The amplitude and phase is then estimated in a recursive, Kalman filter process that minimizes the mean square error between the model and the measured tissue harmonic motion as indicated above in equations (14)-(18). As indicated by process block 205, the change in tissue oscillation phase as a function of distance is then calculated for this beat frequency using the calculated phase values at the 11 points along the artery.

The above process is repeated for each of the prescribed beat frequencies. When used for measuring artery stiffness, vibration frequencies of 100, 200, 300, 400 and 500 Hz are employed, and data acquisition continues until all frequencies have been acquired as determined at decision block 206.

As indicated at process block 208, the next step is to calculate the shear wave speeds in the subject tissue 21 at the different beat frequencies. Linear regression is applied to the 11 phase changed measurements to yield a phase change over 10 mm distance along the artery. From this phase change over distance information, the shear wave speed at each beat frequency is estimated as described by equation (37).

As indicated at process block 210, the final step is to calculate a mechanical property of the tissue 21 from the shear wave speed information. In the preferred embodiment the shear elasticity and viscosity of the tissue 21 is estimated from the set of shear wave speeds. These mechanical properties indicate the stiffness of the artery which is a valuable clinical measurement. This calculation is based on shear wave dispersion, and as described by S. Chen et al "Complex Stiffness Quantification Using Ultrasound Stimulated Vibrometry", 2003 IEEE Ultrasonics Symposium 941-944, the shear wave speeds at multiple frequencies are fit with appropriate theoretical models to solve for the shear elasticity and viscosity.

While the analysis of the received echo signal is performed in the mid-processor section of an ultrasound receiver in the preferred embodiment described above, it should be apparent that these functions can also be performed in a separate processor or computer workstation.

The invention claimed is:

1. A vibro-acoustic system which comprises:
    a) a force generator for imparting harmonic motion to a subject at a prescribed frequency, the harmonic motion propagating over a given distance;
    b) an ultrasonic system including:
    an ultrasonic transducer;
    a transmitter connected to the ultrasonic transducer and being operable therewith to produce an ultrasonic beam which repeatedly applies ultrasonic energy to each of a plurality of spaced apart prescribed points on the subject through which the imparted harmonic motion propagates;
    a receiver connected to the ultrasonic transducer and being operable therewith to receive from each of the spaced apart prescribed points a corresponding plurality of ultrasonic echoes; and
    c) a processor connected to receive the ultrasonic echoes and including a Kalman filter which for each of the spaced apart prescribed points extracts from the corresponding plurality of ultrasonic echoes an amplitude and a phase of the harmonic motion at that prescribed point, and wherein the processor is operable to calculate a mechanical property using the extracted information.

2. The system as recited in claim 1 in which the receiver operates to produce quadrature I and Q signals from each plurality of ultrasound echoes and the Kalman filter receives the quadrature I and Q signals.

3. The system as recited in claim 1 in which the subject is tissue and the mechanical property is complex stiffness.

4. A method for measuring a mechanical property of a subject, the steps comprising:
    a) applying a force to the subject which imparts harmonic motion thereto at a prescribed frequency, the harmonic motion propagating over a given distance;
    b) sensing the harmonic motion at a plurality of spaced apart prescribed points on the subject, through which the harmonic motion propagates, with an ultrasonic system that applies a pulsed ultrasonic beam to each prescribed point and receives a corresponding plurality of ultrasonic echo signals from each prescribed point;
    c) processing the corresponding plurality of ultrasonic echo signals to detect the harmonic motion at each of the prescribed points and to extract a phase of the harmonic motion at each of the prescribed points;
    d) calculating the mechanical property using the extracted phases.

5. The method as recited in claim 4, wherein the subject is tissue.

6. The method as recited in claim 4, wherein the mechanical property is one of shear elasticity and viscosity.

7. The method as recited in claim 4 in which step c) includes:
    i) demodulating the received ultrasonic echo signals to produce quadrature I and Q signals;
    ii) calculating the arctangent of the ratio of said I and Q signals; and
    iii) filtering the signal which results from step ii) with a Kalman filter to extract the phase of the harmonic motion therein at the prescribed frequency.

8. A method for measuring a mechanical property of a subject, the steps comprising:
    a) applying a force to the subject which imparts harmonic motion thereto at a prescribed frequency;
    b) sensing the harmonic motion at a plurality of prescribed points on the subject with an ultrasonic system that repeatedly applies a pulsed ultrasonic beam to each prescribed point and receives a corresponding plurality of ultrasonic echo signals from each prescribed point;
    c) processing the corresponding plurality of ultrasonic echo signals to detect the harmonic motion at each of the prescribed points and to extract a phase of the harmonic motion at each of the prescribed points;
    d) calculating a first shear wave speed using the extracted phases at the prescribed points;
    e) repeating steps a) through c) at a different prescribed frequency and calculating a second shear wave speed using the extracted phases at the prescribed points at the different prescribed frequency; and
    f) calculating the mechanical property using the first wave speed and the second wave speed.

9. The method as recited in claim 8 in which the subject is tissue.

10. The method as recited in claim 8 wherein step e) is repeated a plurality of times to calculate a plurality of corresponding shear wave speeds and the mechanical property is calculated using all the calculated shear wave speeds.

11. The method as recited in claim 8 in which the mechanical property is one of shear elasticity and viscosity.

12. The method as recited in claim 8 in which both shear elasticity and viscosity are calculated using the first wave speed and the second wave speed.

13. The method as recited in claim 8 in which steps b) and c) include:
    i) demodulating received ultrasonic echo signals to produce quadrature I and Q signals;
    ii) calculating the arctangent of the ratio of said I and Q signals; and
    iii) filtering the signal which results from step ii) using a Kalman filter to extract a phase of the harmonic motion therein at the prescribed frequency.

14. The method as recited in claim 13, further including modeling a desired harmonic signal representative of the harmonic motion by a differential equation and recursively estimating the amplitude and the phase of the harmonic motion at each of the prescribed points using the Kalman filter.

15. The method as recited in claim 8 in which step a) includes applying an acoustic force to the subject.

* * * * *